United States Patent
Chen et al.

(10) Patent No.: US 8,235,975 B2
(45) Date of Patent: *Aug. 7, 2012

(54) LIGHT TRANSMISSION SYSTEM FOR PHOTOREACTIVE THERAPY

(75) Inventors: James C. Chen, Clyde Hill, WA (US); Steven R. Daly, Sammamish, WA (US); Zihong Guo, Bellevue, WA (US); Llew Keltner, Portland, OR (US); Jeffrey R. Storm, Issaquah, WA (US)

(73) Assignee: Light Sciences Oncology, Inc., Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/274,192

(22) Filed: Oct. 14, 2011

(65) Prior Publication Data

US 2012/0089207 A1    Apr. 12, 2012

Related U.S. Application Data

(63) Continuation of application No. 11/416,783, filed on May 3, 2006, now Pat. No. 8,057,464.

(51) Int. Cl.
*A61B 18/18* (2006.01)

(52) U.S. Cl. ............. 606/14; 606/10; 606/13; 607/88; 607/89

(58) Field of Classification Search .............. None
See application file for complete search history.

(56) References Cited

U.S. PATENT DOCUMENTS

| 4,128,173 | A | | 12/1978 | Lazarus et al. | |
|---|---|---|---|---|---|
| 4,408,263 | A | * | 10/1983 | Sternlicht | 362/189 |
| 4,522,302 | A | | 6/1985 | Paikoff | |
| 5,445,608 | A | * | 8/1995 | Chen et al. | 604/20 |
| 5,634,921 | A | * | 6/1997 | Hood et al. | 606/5 |
| 5,851,221 | A | * | 12/1998 | Rieder et al. | 607/93 |
| 6,162,214 | A | * | 12/2000 | Mueller et al. | 606/15 |
| 6,210,425 | B1 | | 4/2001 | Chen | |
| 6,273,904 | B1 | * | 8/2001 | Chen et al. | 607/88 |

(Continued)

FOREIGN PATENT DOCUMENTS

EP    1262179    12/2002

(Continued)

OTHER PUBLICATIONS

PCT International Search Report, counterpart PCT Application PCT/US2006/018570, mailed Mar. 4, 2008, 5 pages.

(Continued)

*Primary Examiner* — Henry M Johnson, III
*Assistant Examiner* — Lynsey Crandall
(74) *Attorney, Agent, or Firm* — Perkins Coie LLP

(57) ABSTRACT

A light transmission system to provide photodynamic treatment to a patient includes a single use integrated control module and catheter assembly having a plurality of light emitting diodes (LEDs) to transmit light toward target cells within a patient. The integrated light catheter and control module are used in combination with a light activated drug. Selected operating parameters may be programmed into the control module, or it may be wirelessly programmable in situ prior to use to allow user flexibility to tailor treatment for a particular patient or condition. Among the features that prevent reuse are that the control module lacks access to recharge the power source, and it may include a deactivation module that destroys circuitry or software when triggered. To prevent patient interference when in use, the control module may also be configured to selectively deactivate.

17 Claims, 9 Drawing Sheets

U.S. PATENT DOCUMENTS

| | | |
|---|---|---|
| 6,350,772 B1 | 2/2002 | Kuroiwa et al. |
| 6,416,531 B2 | 7/2002 | Chen |
| 6,445,011 B1 | 9/2002 | Hirano et al. |
| 6,454,789 B1 | 9/2002 | Chen et al. |
| 6,602,274 B1 | 8/2003 | Chen |
| 6,661,167 B2 | 12/2003 | Eliashevich et al. |
| 6,689,380 B1 * | 2/2004 | Marchitto et al. ............ 424/449 |
| 6,784,460 B2 | 8/2004 | Ng et al. |
| 6,899,723 B2 | 5/2005 | Chen |
| 6,958,498 B2 | 10/2005 | Shelton et al. |
| 7,015,240 B2 | 3/2006 | North et al. |
| 8,057,464 B2 | 11/2011 | Chen et al. |
| 2001/0049502 A1 | 12/2001 | Chen |
| 2003/0065315 A1* | 4/2003 | Hareyama et al. .............. 606/11 |
| 2003/0114434 A1 | 6/2003 | Chen et al. |
| 2004/0122419 A1* | 6/2004 | Neuberger ...................... 606/10 |
| 2005/0070976 A1* | 3/2005 | Samuel et al. .................. 607/88 |
| 2005/0113815 A1* | 5/2005 | Ritchie et al. ................... 606/15 |
| 2005/0187597 A1 | 8/2005 | Vanderschuit |
| 2005/0228260 A1 | 10/2005 | Burwell et al. |
| 2005/0279354 A1 | 12/2005 | Deutsch et al. |
| 2006/0129211 A1* | 6/2006 | Canitano et al. ................ 607/89 |
| 2006/0265031 A1* | 11/2006 | Skwarek et al. ................ 607/88 |
| 2006/0282132 A1* | 12/2006 | Arai et al. ....................... 607/88 |
| 2007/0002582 A1 | 1/2007 | Burwell et al. |
| 2007/0260295 A1* | 11/2007 | Chen et al. ...................... 607/88 |

FOREIGN PATENT DOCUMENTS

| | | |
|---|---|---|
| EP | 1334748 | 8/2003 |
| EP | 2059302 B1 | 7/2010 |
| HK | 1128252 | 10/2010 |
| JP | 2004148124 A | 5/2004 |
| JP | 2005124889 A | 5/2005 |
| JP | 2009535151 | 10/2009 |
| TW | 200742568 | 11/2007 |
| WO | WO-97/04836 | 2/1997 |
| WO | WO-02/41364 | 5/2002 |
| WO | WO-03/005923 | 1/2003 |
| WO | WO-03/043697 A2 | 5/2003 |
| WO | WO-2004/093760 | 11/2004 |
| WO | WO-2007130072 | 11/2007 |

OTHER PUBLICATIONS

International Searching Authority, Written Opinion, counterpart PCT Application PCT/US2006/018570, mailed Nov. 4, 2008, 13 pages.

* cited by examiner

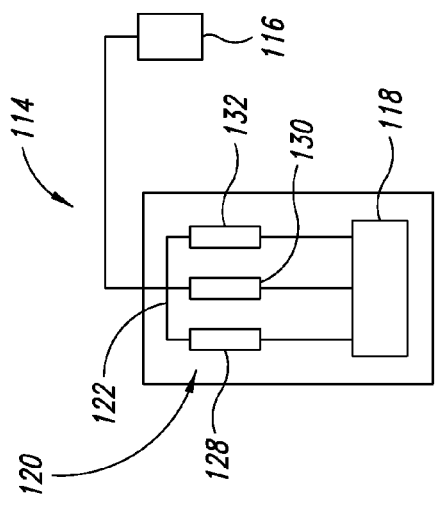
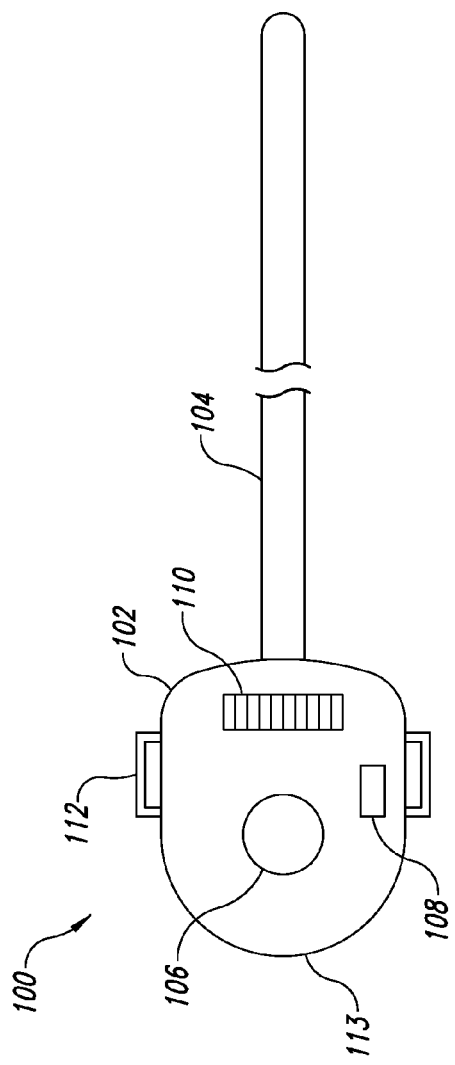
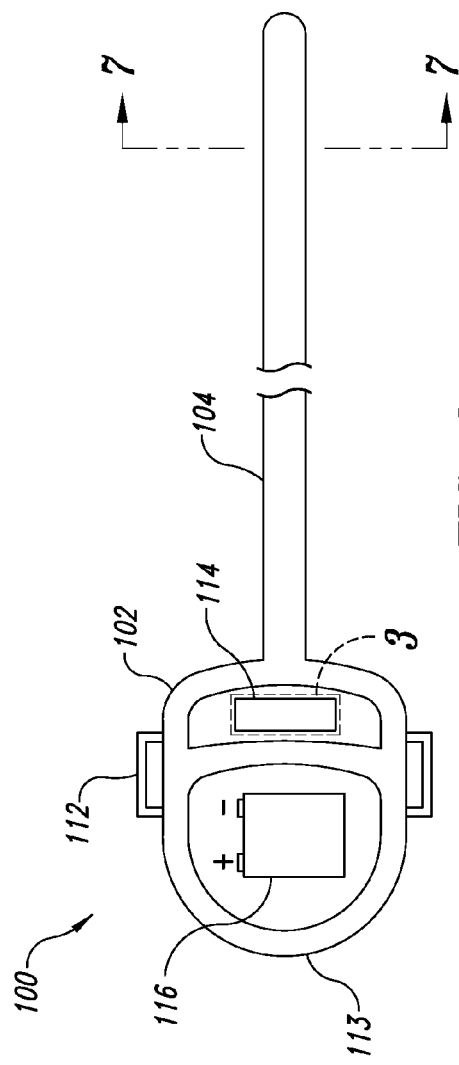

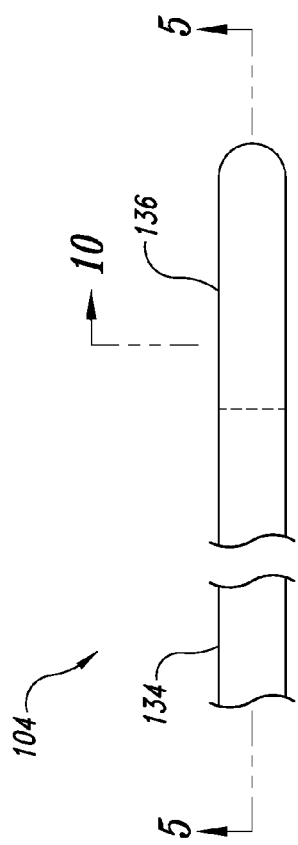
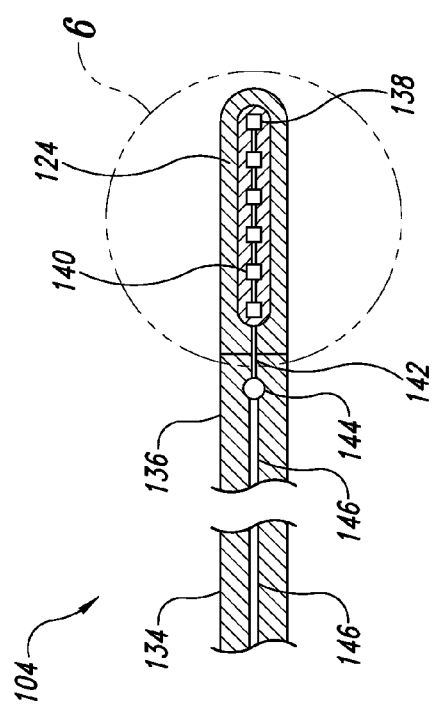
FIG. 4
FIG. 5

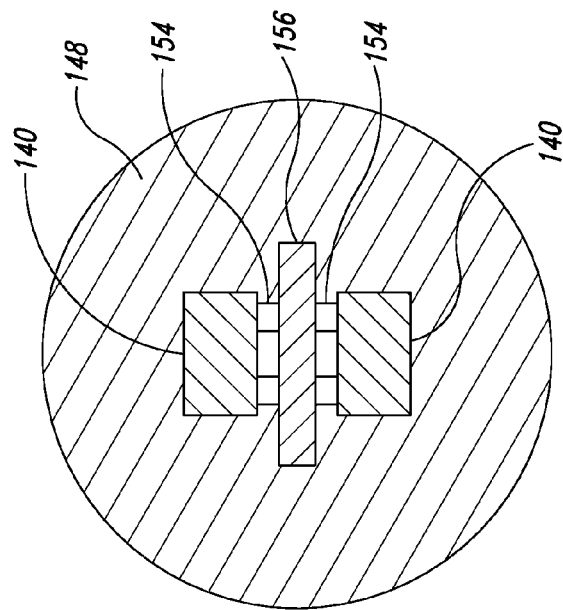
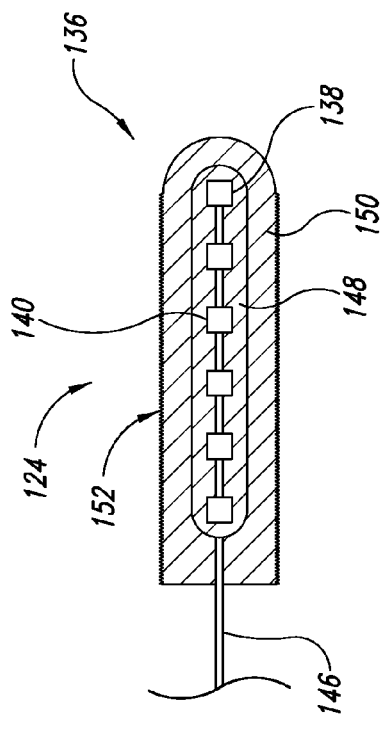
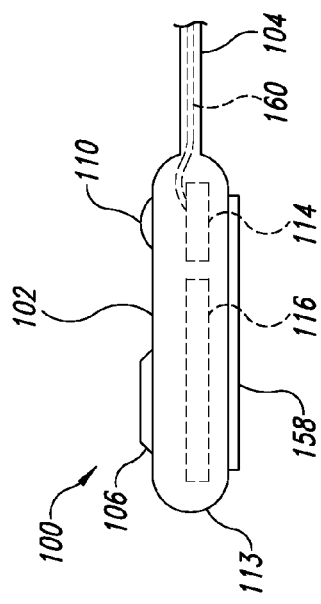

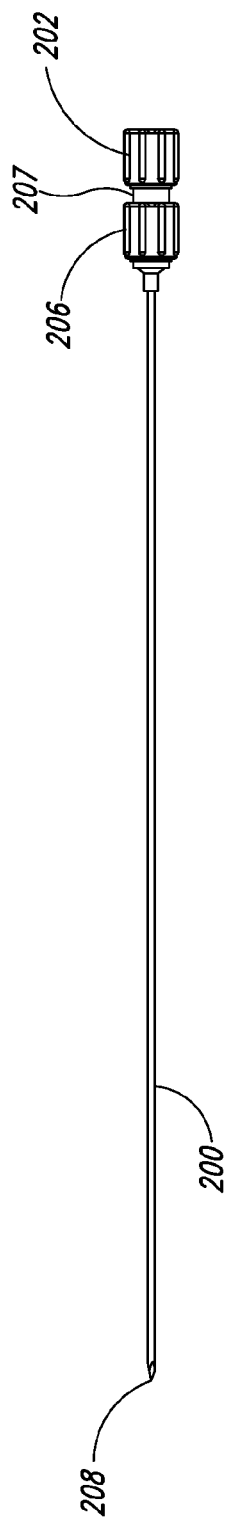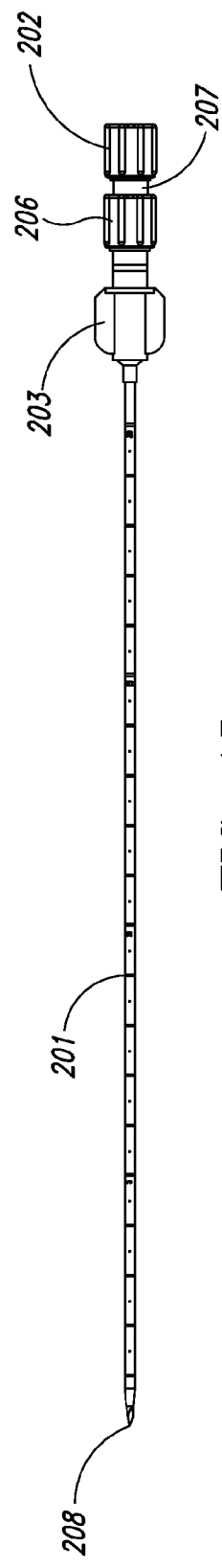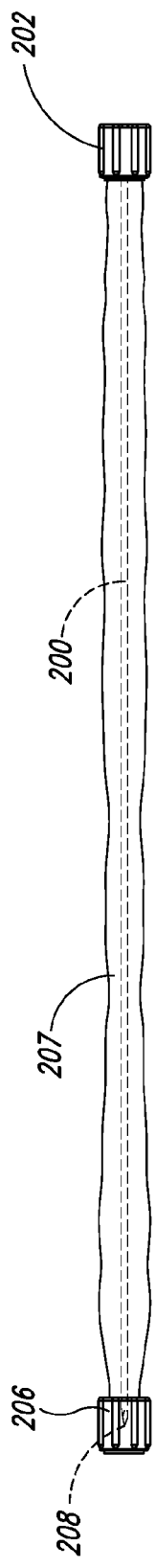
FIG. 14
FIG. 15
FIG. 16

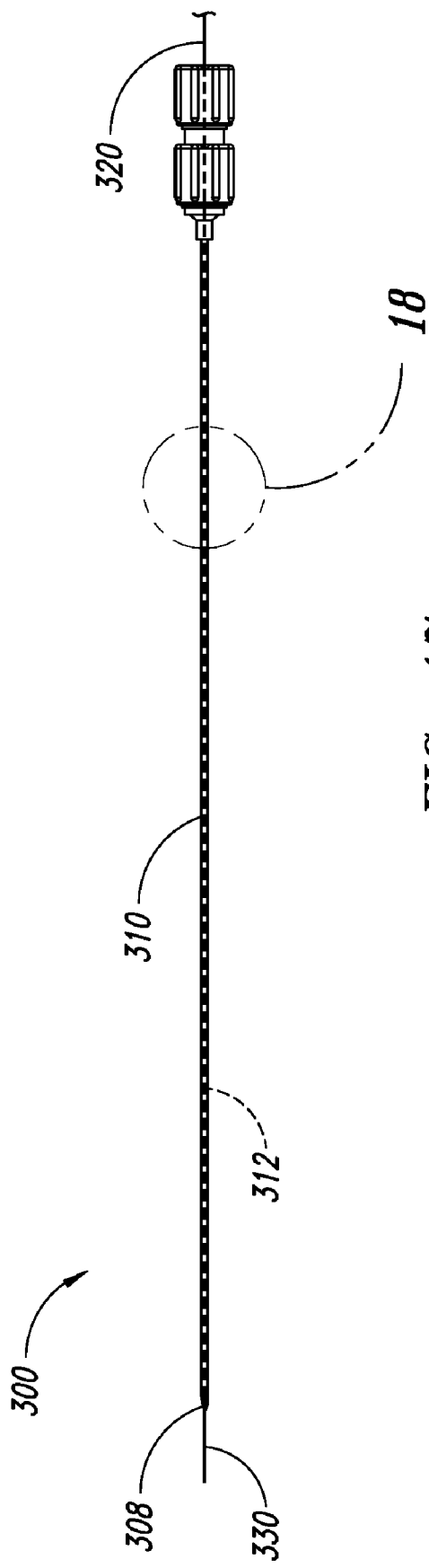
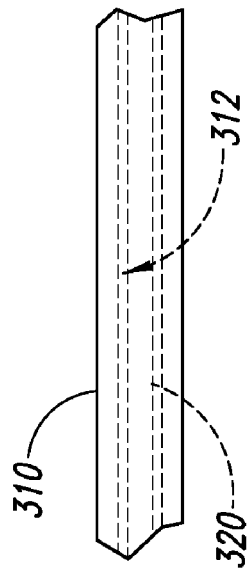
FIG. 17
FIG. 18

LIGHT TRANSMISSION SYSTEM FOR PHOTOREACTIVE THERAPY

CROSS-REFERENCE TO RELATED APPLICATION

This application is a continuation of U.S. patent application Ser. No. 11/416,783, filed May 3, 2006, now pending, which application is incorporated herein by reference in its entirety.

BACKGROUND OF THE INVENTION

1. Field of the Invention

The present invention relates generally to a light transmission system for medical treatment, such as photodynamic therapy, in combination with a photoactive drug.

2. Description of the Related Art

In photodynamic therapy (PDT), light of a specific wavelength or waveband is directed toward a target cell or cells that have been rendered photosensitive through the administration of a photoreactive, photoinitiating, or photosensitizing agent. This photoreactive agent has one or more characteristic light absorption wavelengths of which at least one has a large peak. The large peaks occur at "excitation wavelengths" that may be useful in PDT. The drug is commonly administered to a patient via intravenous injection, oral administration, or by local delivery to the treatment site. Once the photoactive agent has associated itself with abnormal cells, the abnormal cells can be treated by exposure to an appropriate excitation wavelength of the photoreactive agent.

The objective of PDT may be either diagnostic or therapeutic. In diagnostic applications, the wavelength of light is selected to cause the photoreactive agent to fluoresce as a means to acquire information about the targeted cells without damaging the targeted cells. In therapeutic applications, the wavelength of light delivered to the targeted cells treated with the photoreactive agent causes the agent to undergo a photochemical reaction with oxygen in the targeted cells to yield free radical species (such as singlet oxygen), which in turn cause any or all of cell lysis, cell necrosis, and occlusion of (new) blood vessels.

One type of light delivery system used for PDT treatments comprises the delivery of light from a light source, such as a laser, to the targeted cells using an optical fiber delivery system with special light-diffusing tips on the fibers. This type of light delivery system may further include optical fiber cylindrical diffusers, spherical diffusers, micro-lensing systems, an over-the-wire cylindrical diffusing multi-optical fiber catheter, and a light-diffusing optical fiber guide wire. This light delivery system generally employs a remotely disposed high-powered laser, or solid state laser diode array, coupled to optical fibers for delivery of the light to the targeted cells.

The light source for the light delivery system used for PDT treatments may also be light emitting diodes (LEDs). LEDs may be arrayed in an elongate device to form a "light bar" for the excitation light delivery system. The LEDs may be either wire bonded or electrically coupled utilizing a "flip chip" technique that is used in arranging other types of semiconductor chips on a conductive substrate. Various arrangements and configurations of LEDs are described in U.S. Pat. Nos. 6,958,498; 6,784,460; and 6,445,011.

Several devices shown in the literature are intended for use in photodynamic therapy and generate light inside the body, once inserted. For example, U.S. Pat. No. 5,445,608 depicts a flexible array of light transmitters that are inserted transcutaneously. These devices are reusable, generally, and have features while apparently offering cost reduction, also poses risks: infection due to improper sterilization, and improper treatment due to potential undetected failure of some of the reused light transmitters in the arrays. In addition, in reuse of most equipment, there are additional parts and labor costs in servicing and maintaining the equipment.

One of the challenges in design and production of light bars relates to size: large diameter light bars cause significant trauma to tissue through which it passes, and have potentially painful effects for the patient. However, light bar size is dictated by several factors including the size of light emitters that emit light of wavelength desired at a sufficient energy level, and the fragility of the bar as its thickness is reduced which increases risk of breaking in the patient. Accordingly, there is a need for smaller high powered LEDs, thinner light bars that are not too fragile for safe use for their intended purpose, and a device that is single use after removal from a sterile pack, and conveniently supplied with an appropriate amount of a photoactive agent.

BRIEF SUMMARY OF THE INVENTION

The invention provides devices, methods and kits related to a light transmission system that provides photodynamic treatment to a patient.

In general, the light transmission device includes a control module and a catheter assembly. In one embodiment, the control module and catheter assembly are fused together, and not intended for separation. The device is lightweight, portable, and disposable and configured for only a single use. This single use feature imparts significant advantages: the device is always sterile, and suffers none of the potential contamination risks of reusable devices. In addition, end user costs are reduced: there are no serviceable parts requiring skilled labor and no equipment is required to sterilize or recharge the device. Further, the flexible catheter of the device has a small exterior dimension with a distal end containing a light emitting array. The small dimension minimizes tissue trauma upon insertion of the catheter into the patient. The device can be delivered in a sterile pack kit along with an appropriate photoactive agent dose so that it is convenient for certain types of procedures, and facilitates treatment in a non-surgical environment leading to potential reduction in costs.

In one embodiment, the invention provides a single use device that includes a sealed control module with an internal power source and programmable circuitry. It has a catheter assembly extending from and fused to the control module to form an integral unit. The catheter assembly includes light transmitting devices in electrical communication with the power source. The device includes a power depletion system in communication with the power source to selectively deplete energy from the power source.

In another embodiment, the invention provides a single use device that includes a sealed control module with an internal power source and programmable circuitry. It has a catheter assembly extending from and fused to the control module to form an integral unit. The catheter assembly includes light transmitting devices in electrical communication with the power source. The device includes a deactivation module for selectively disabling the device after a single use.

Another embodiment of the invention is a sterile, packaged surgical kit for administering photoreactive therapy to a patient. The kit includes several features: a portable, single use, sealed control module that contains a power source and control circuitry in communication with the power source;

and a polymeric, flexible catheter assembly extending from a first end fused to the control module to a second end that has encapsulated therein a light transmission array that is in electrical communication with the power source. The light array includes a plurality of LEDs and the catheter assembly has an outer dimension of about 0.8 to about 1.5 mm. The LEDs have a height in the range from about 0.152 to about 0.304 mm. In addition, the kit contains a surgical sheath that has a lumen adapted to receive the catheter assembly. The sheath is made of a flexible polymeric material and has a lumen with an inner diameter adapted to accept a portion of the catheter assembly. The sheath has an introduced parting line along a length thereof and an outward extending member configured for manual grasping and pulling to split the sheath along the parting line. Also included in the kit is a container with a quantity of a photoreactive agent such as mono-L-aspartyl chlorin $e_6$ sufficient to administer a single dose to a patient. At least the control module, catheter assembly, and surgical sheath are enclosed within a sterile package.

The invention also provides methods of administering photoactive therapy to treat targeted tissue of a human or non-human patient. In one embodiment the method includes identifying a location of abnormal tissue to be treated; transcutaneously inserting into a body of the patient a trocar disposed within a surgical sheath, and guiding the sheath to a position proximate the location of the abnormal tissue. Further, it includes withdrawing the trocar from the sheath while retaining the sheath in position. Before, during or after trocar inserting, the method includes administering an effective dose of a photoactive composition to the patient. After trocar withdrawal from the sheath, the method includes inserting at least an end portion of a catheter assembly into the sheath, where the catheter assembly is fused to a sealed single use control module, and the control module contains a power source and control circuitry configured to carryout a treatment protocol. The catheter assembly end portion comprising a light transmission array. Then, the method requires activating the control module, preferably after confirming placement of the light transmission array of the catheter assembly relative to abnormal tissue to be treated. And, automatically terminating light treatment after a predetermined period of treatment.

In some embodiments, the light-activated drug is mono-L-aspartyl chlorin $e_6$, also referred to herein as Talaporfin Sodium. This compound has an absorption spectrum that exhibits a maximum peak at the excitation wavelength of 664 nm, which is the wavelength favored when it is used in photoreactive therapy.

BRIEF DESCRIPTION OF THE DRAWINGS

The following drawings are intended as an aid to an understanding of the invention and to present examples of the invention, but do not limit the scope of the invention as described and claimed herein. In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility.

FIG. 1 is an elevational side view of a first side of a light transmission system having a control module and a catheter assembly, according to one illustrated embodiment of the invention.

FIG. 2 is an elevational side view of another side of the light transmission system of FIG. 1.

FIG. 3 is a schematic view of a controller located in the control module of the light transmission system of FIG. 1.

FIG. 4 is a partial side elevational view of the catheter assembly of FIG. 1.

FIG. 5 is a cross-sectional elevational view of the catheter assembly taken along line 5-5 of FIG. 4 where the catheter assembly includes an encapsulated light array.

FIG. 6 is a detailed, cross-sectional view of the encapsulated light array of FIG. 5.

FIG. 7 is a detailed, cross-sectional view taken along line 7-7 of FIG. 1 illustrating one technique of arranging a pair of LEDs.

FIG. 8 is a top plan view of the light transmission system of FIG. 1 that includes a fiber optic waveguide coupled to the control module according to one embodiment.

FIG. 14 is a side elevational view of a trocar provided in accordance with one embodiment of the present invention.

FIG. 15 is a side elevational view of the trocar of FIG. 14 inserted into a surgical sheath in accordance with one embodiment of the present invention.

FIG. 16 is a side elevational view of the trocar after it has been used to insert the sheath into a surgical site of the patient.

FIG. 17 is a side elevational view of a delivery assembly provided in accordance with one embodiment of the present invention.

FIG. 18 is a detailed side elevational view of the delivery assembly of FIG. 17 where the delivery assembly includes a guide wire disposed within a needle.

DETAILED DESCRIPTION OF THE INVENTION

Figure 9:
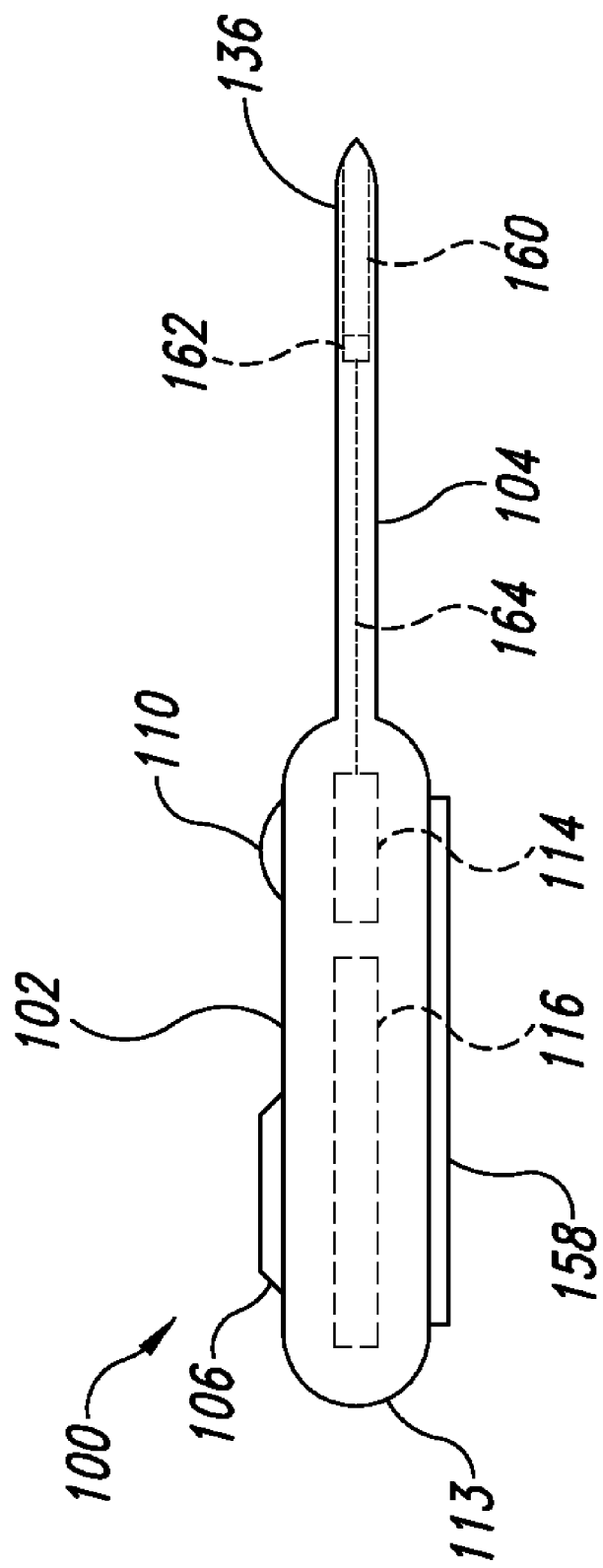
FIG. 9 is a top plan view of the light transmission system of FIG. 1 that includes a fiber optic waveguide coupled to the control module according to an alternative embodiment than illustrated in FIG. 8.

The following detailed description is merely illustrative in nature and is not intended to limit the invention or the application and uses of the invention. Furthermore, there is no intention to be bound by any expressed or implied theory presented in the preceding technical field, background, or the following detailed description.

The invention may be described herein in terms of functional and/or logical block components and various processing steps. It should be appreciated that such block components may be realized by any number of hardware, software, and/or firmware components configured to perform the specified functions. For example, an embodiment of the invention may employ various integrated circuit components, e.g., memory elements, digital signal processing elements, logic elements, look-up tables, or the like, which may carryout a variety of functions under the control of one or more microprocessors or other control devices. In addition, those skilled in the art will appreciate that the present invention may be practiced in conjunction with any number of data transmission protocols and that the system described herein is merely one exemplary application for the invention.

In the specification and claims, the term "fused" when used with respect to the catheter assembly being connected to the control module should be broadly interpreted to mean that the catheter assembly and control module are sealed together as a single unit. While the catheter and control module may be molded or otherwise fabricated together as an integral single piece, they may also be fabricated initially as two separate components that are subsequently joined together through mechanical fit and adhesive, adhesive alone, or by other means so that subsequent attempts at separation lead to significant impairment or destruction of one or the other or both. The joining may be through direct contact between the catheter and control module or there may be one or more components interposed between them, such as for example a sleeve adhered over the catheter at the end so that the sleeve is joined to the catheter. Regardless of whether contact is direct or there is one or more components interposed between them, the catheter and control module are joined in a manner so that attempts at subsequent separation result in significant impairment or destruction of one or the other or both. Accordingly, they are "fused" together.

In the specification and claims, the term "integral" referring to the control module and catheter assembly as a unit means that the two are fused together.

In the specification and claims, the term "catheter assembly" means the catheter including its internal components such as the array of light transmitting devices, lumens, electrical conductors, and any other ancillaries.

In the specification and claims, the term "thickness" as it refers to a dimension of an LED refers to that dimension that might affect the thickness of the catheter assembly in the region surrounding the array of light emitters, when these are LEDs.

FIGS. 1 and 2 illustrate a light transmission system 100. The light transmission system 100 includes a control module 102 and a catheter assembly 104 extending from and fused to the control module 102.

According to one embodiment, the light transmission system 100 is a single use system, which is disposable after the single use. Neither the control module 102 nor the catheter assembly 104 is intended for reuse. Hence, the light transmission system 100 may include certain deactivation or self-destruct features to prevent the system from being refurbished, reconditioned, or otherwise rendered reusable, as described in more detail below.

The control module 102 includes a start/stop switch 106 to turn the system 100 on and off. The control module 102 may further include a test or diagnostic switch 108, a status indicator panel 110, and/or hand grips 112 extending from or arranged on the housing 113 that encloses the various components of the control module 102. The status indicator panel 110, for example, may include a plurality of LEDs that are either illuminated or not illuminated depending on an operational phase of the system 100.

FIG. 2 shows the system 100 from an opposite view of the first side view shown in FIG. 1. The control module 102 further includes a controller 114 and a power source 116. In one embodiment, the controller 114 is a programmable logic control subsystem (PLC) comprised of control circuitry and a programmable memory that is configured to control a variety of aspects and features of the system 100, some of which are described below in more detail. In one embodiment, the power source 116 is a battery, for example, a lithium battery.

In one embodiment, the device incorporates a wireless or wired interface that allows communication with a PC or other programming device loaded with compatible treatment planning software that computes treatment parameters and transmits these to the power controller via the interface. If a wireless interface is used, it can be of any useful type, including but not limited to infrared diodes, R.F. or low-frequency magnetic coupling, Bluetooth® communication protocol, and the like. The treatment planning software may provide, among other things, optical power settings, light dose and light dose fractionation schedule settings, as will be discussed in greater detail below.

An adhesive may be provided on a patient-facing side of the control module 102 to secure the module to the body of a patient, if the module is intended to be attached to the patient. Alternatively, a double sided adhesive patch may be selectively adhered to the control module and to the patient to secure the module to the patient.

FIG. 3 shows the controller 114 having a control subsystem 118 in communication with one or more memory devices 120. One or more buses 122 link the power source 116, the control subsystem 118, and an illumination subsystem 124 (FIG. 5), which is arranged in the catheter assembly 104. The controller 114 provides control signals over the bus 122 to operate the illumination subsystem 124 and may also process signals received over the bus 122 from a photodiode 162 (FIG. 9), for example. The control subsystem 118 can take a variety of forms, for example one or more microprocessors, Digital Signal Processors (DSPs), Field Programmable Gate Arrays (FPGAs), and/or Application-Specific Integrated Circuits (ASICs).

The memories 120 may take a variety of forms, for example, one or more buffers 128, registers (not shown), random access memories (RAMs) 130, and/or read only memories (ROMs) 132. The buffer 128 may temporarily store data received from the illumination subsystem 124 until the control subsystem 118 is ready to process the data. Typically, the ROM 132 will persistently store instructions and/or data executable by the control subsystem 118. Typically, the RAM 130 will dynamically store instructions and/or data for use by the control subsystem 118.

As illustrated in FIG. 4, the catheter assembly 104 has a proximal portion 134 and a distal portion 136 relative to the control module 102. As illustrated in FIG. 5, the distal portion 136 of catheter assembly 104 includes a light transmission array 138. In one embodiment, the light transmission array 138 comprises a plurality of LEDs 140 in electrical communication via a conductive connector 142 according to the illustrated embodiment. The conductive connector 142 may be selected from any suitable conductor that can be accommodated within the dimensions of the catheter, for example: a bus bar that electronically couples the LEDs to the controller 102; flexible wires; a conductive film or ink applied to a substrate, and the like. Additionally or alternatively, the light transmission array 138 may include Bragg reflectors to better control the wavelength of the light that is to be transmitted to the target cells.

The controller 102 may be programmed to activate and deactivate LEDs 140 of light transmission array 138 in a pulsed sequence. For example, the LEDs may form two halves of the light array that may be turned on and off independently from each other. Alternatively, the system may be programmed to selectively activate and deactivate different selected individual or groups of LEDs along the length of the bar. In this manner, a treatment protocol, for example causing the LEDs to be lit in a certain sequence, at a particular power level for a selected period of time, may be programmed into the controller 102. Therefore, by selectively timing the pulses of light, the system delivers light in accordance with a selected drive form program.

Without being bound by any theory, applicants believe that by delivering light in pulses, the efficacy of the PDT is improved, given that the treated tissue is allowed to reoxygenate during the cycles when the light is off. Applicants further believe that tissue oxygenation during therapy is improved by using a lower frequency. In one embodiment the operational frequency is 50 Hz-5 kHz, and in one embodiment, is 50-70 Hz.

The catheter assembly 104 may optionally include a deactivation and/or destruct module 144 as mentioned above, as one means of disabling the operation of the system 100 if and when a certain condition is present. For example, the deactivation module 144 may cause the system 100 to at least temporarily shut down if a potentially harmful condition to a patient and/or a potentially damaging condition to the system 100 (e.g., overheating, electrical short, etc.) is detected. Additionally or alternatively, the deactivation module 144 may cause the system 100 to be permanently inoperable after the single use. Determining the duration of the single use may be accomplished by using a timer or an appropriate type of sensor such as a heat, pressure, light, or other sensor, for example. In one embodiment, the deactivation module 144 includes a chemical fuse, which after receiving a deactivation signal, operates to destroy at least a portion of a conductive connection 146 extending between the controller 102 and the light transmission array 138. It is appreciated that in the absence of the deactivation module 144, the conductive connection 146 may extend from the control module 102 to the light transmission array 138. Further, it is appreciated that the conductive connection 146 may be structurally similar to the conductive connector 142 located in the light transmission array 138. While FIG. 5 shows an example of a deactivation module 144 to be located within the catheter 104, it could of course be located elsewhere, as long as it is able to disrupt supply of electrical energy to the light transmission array 138.

In accordance with the present invention, the control circuitry further includes the capability to completely discharge or deplete the battery, to allow safe disposal of the device. This reduces the fire hazard and cost, for example, for hospitals that are responsible for the disposal of such devices. While this may be accomplished in any of a variety of ways, in one embodiment, low impedance is applied across the battery. Such depletion may be programmed into the system to be auto triggered upon the occurrence of a selected event, or it may be user activated. To further prevent reuse of the device, the software can be configured to perform a self-erase function at the end of therapy, leaving only the battery discharge function working. For example, it might trigger a worm or virus that deletes software programming and that also removes the capability to re-program through interface with an appropriately configured computer, for example, as discussed above.

In one embodiment, the drive circuit is capable of producing constant current D.C., A.C., square wave and pulsed wave drive signals. This is accomplished by combining a constant source with a programmable current steering network allowing the controller 102 to selectively change the drive wave form. For example, the steering network may be modulated to achieve the various functions described above, for example, producing the desired impedance to fully discharge the battery. Furthermore, use of an A.C. drive allows for a two-wire connection to the LEDs, thereby reducing the cross-sectional diameter of the catheter, while still permitting use of two back-to-back emission sources, that when combined, produce a cylindrical light source emission pattern.

Therefore, as discussed above, the light transmission system 100 comprises a unitary, single use disposable system for PDT. It should be noted that in certain embodiments the catheter is fused to the control module to form an integrated single unit. Any attempt to disconnect the catheter in this embodiment results in damage to either the catheter, or module, or both.

According to one embodiment, the light transmission system is used in connection with any light-activated drug of which there are many known in the art and some of which are listed in U.S. Pat. No. 7,015,240 which is fully incorporated by reference with regard to disclosed photoactive compositions. In one particular embodiment, the light-activated drug is Talaporfin Sodium. Talaporfin Sodium is a chemically synthesized photosensitizer, having an absorption spectrum that exhibits a maximum peak at 664 nm. In one embodiment, the Talaporfin Sodium is presented as a lyophilized powder for reconstitution. One hundred milligrams of Talaporfin Sodium is reconstituted with 4 milliliters of 0.9% isotonic sterile sodium chloride solution, to give a solution at a concentration of 25 mg/ml.

A dose of Talaporfin Sodium is administered intravenously to the patient at 1 mg/kg, over a period of 3 to 5 minutes. After, during or before administration of the selected photoactive composition in an appropriate dose, the light catheter is positioned within a patient at a preselected location appropriate to treat tissue to be treated. Preferably, the catheter is inserted transcutaneously under guidance of either ultrasound, CT or another suitable imaging technique to ensure appropriate juxtaposition of the light transmission array 138 relative to the tissue to be treated.

The drug must be activated with light, and light energy is measured here in Joules (J) per centimeter of length of the light transmitting array. Likewise the fluence of light is measured in milli-watts (mW) per centimeter of length of the light emitting array. Clearly, the amount of energy delivered will depend on several factors, among them: the photoactive agent used, the dose administered, the type of tissue being treated, the proximity of the light array to the tissue being treated, among others. The energy (E) delivered is the product of the fluence (F) and the time period (T) over which the fluence is delivered: $E=F \times T$. The fluence may be delivered for only a fraction of the treatment time, because the light array may be pulsed, for example in a frequency such as 60 kHz, or may be controlled by a timing pattern. An example of a timing pattern is that the array is at full fluence for 20 seconds, then off for 10 seconds in a repetitive cycle. Of course, any pattern and cycle that is expected to be useful in a particular procedure may be used. The control module is programmable in many embodiments for such fractionated light delivery.

In accordance with an embodiment, fifteen minutes to one hour following Talaporfin Sodium administration, light energy in the range from about 50 to about 1000 J/cm of light array fluence in the range from about 5 to about 50 mW/cm of light array is delivered to the treatment site. As may be expected, the equation discussed above relating energy time and fluence plays a role in selection of the fluence and energy delivered. For example, depending upon the patient, a certain time period may be selected as suitable. In addition, the nature of treatment might dictate the energy required. Thus, fluence F is then determined by $F=E/T$. The light array should be capable of providing that fluence in the allotted time period. For example, if a total of 200 J/cm of light array must be delivered to the treatment site at 20 mW/cm of light array, then the treatment period is approximately 2.8 hours.

In embodiments of the invention the control module is programmable for these types of calculations (or the relationships may be "hard wired" or "burned" into the controller)

and is able to set a treatment period T after which the device is automatically turned of and treatment terminates.

Figure 11:
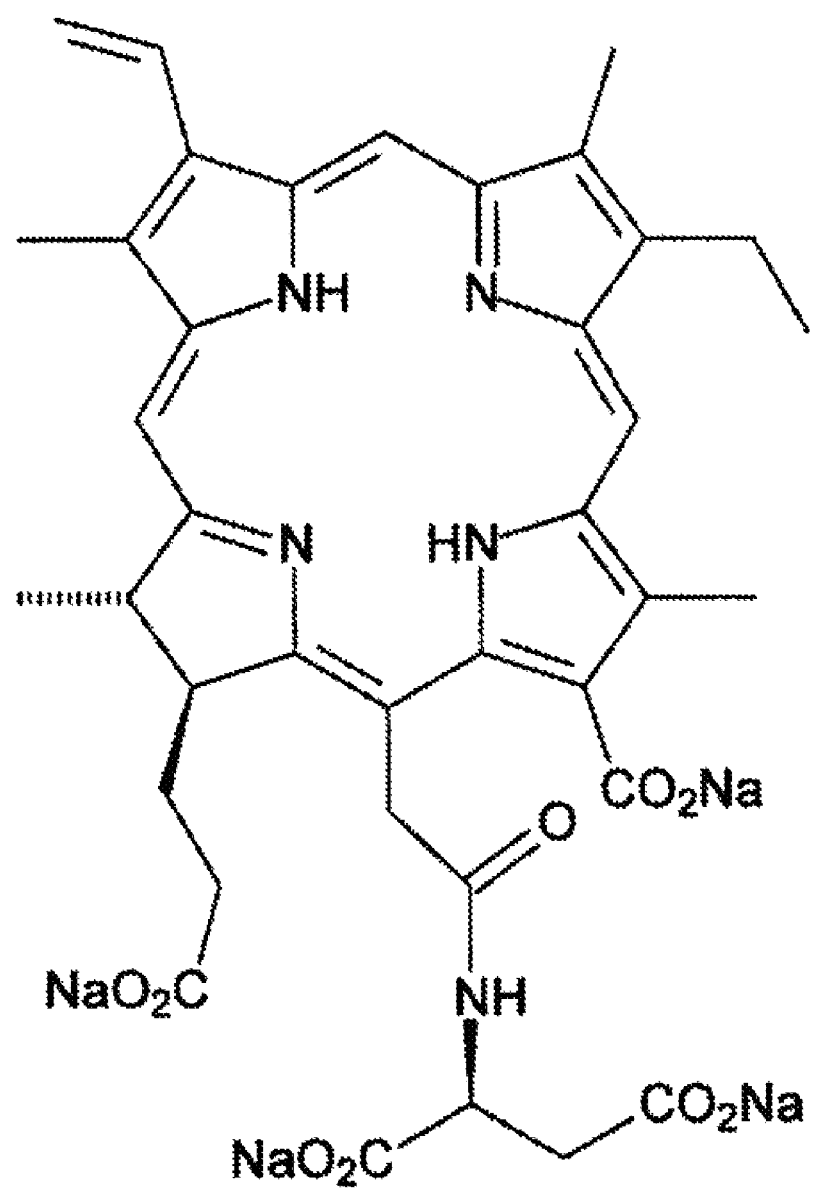
FIG. 11 is an illustration of the structural formula for a light-activated drug used in one embodiment, namely, mono-L-aspartyl chlorin $e_6$ (Talaporfin Sodium).

In one embodiment, the LEDs provided in the catheter assembly emit light with a peak wavelength at 660 nm±5 nm. More than 80% of the power output is within ±20 nm of the peak wavelength, namely the light catheter emits light at a wavelength of about 640-680 nm. The spectral bandwidth of the LED provides a significant overlap with the Talaporfin Sodium absorption curve in the 660 nm region. The structural formula of Talaporfin Sodium is shown in FIG. 11.

To ensure that the treatment protocol is carried out as desired once initiated, the control circuitry may be programmed to preclude patient interference. For example, the controls may be locked once the treatment is initiated, only allowing the physician to stop the treatment, for example, via a code, e.g., by depressing a combination or series of buttons on the controller.

Typically, a light transmission array is encapsulated in a polymeric composition, to protect the LEDs, to protect tissue from direct contact with the LEDs and to allow appropriate modulation of the light emitted. For the very thin light arrays of the invention, which are strong yet flexible, the selection of an appropriate polymer is important. It should be safe for insertion into the body of a patient and should be sufficiently strong and flexible to present little risk of breakage. In addition, it should not interfere with light transmission in the wavelength necessary to activate the photoactive agent. One such polymer is the medical grade epoxy resin 301-2FL obtainable from Epoxy Technology of Billerica, Mass. Other medical grade polymers, upon testing, may also meet these requirements.

FIG. 6 shows a detailed view of the distal portion 136 of the catheter assembly 104 and, in particular, shows a detailed view of the light transmission array 138 encapsulated by a first or inner encapsulant 148 having a first index of refraction $\eta 1$ and over molded by a second or outer encapsulant 150 having a second index of refraction $\eta 2$. It is understood that the "index of refraction," as used herein, is the factor by which the phase velocity of electromagnetic radiation is slowed relative to a vacuum and is usually identified by the Latin symbol q.

One approach to encapsulating the LEDs 140 comprising the light transmission array 138 is to select the first index of refraction of the inner encapsulant 148 to be approximately equal, or equal, to an index of refraction for the substrate material that is used in the construction of the LEDs 140. Some of the more commonly known substrate materials for LEDs are GaN, AlGaN, InGaN, AlInGap and/or AlInGaN. In one embodiment, the inner encapsulant has an index of refraction of 1.51-2.0, and more particularly in one embodiment, is 1.51. The inner encapsulant 148 is typically made from a substantially transparent material that allows for the transmission of light therethrough, such as an optical epoxy or another type of flexible polymer or thermoplastic material.

In accordance with an embodiment of the present invention, the second index of refraction $\eta 2$ is selected to be approximately equal to an index of refraction of the target cells in the surrounding tissue. In one embodiment, the second index of refraction $\eta 2$ of the outer encapsulant 150 is selected to be lower than the first index of refraction $\eta 1$ of the inner encapsulant 148. It is appreciated that it is practically difficult to match or substantially match the second index of refraction $\eta 2$ of the outer encapsulant 150 to the index of refraction of the target cells, thus the objective is to at least match the second index of refraction $\eta 2$ of the outer encapsulant 150 to be as practically close as possible to the index of refraction of the target cells. In one embodiment, the outer encapsulant has an index of refraction of 1.33-1.5. In one embodiment, a maximum thickness or outer dimension of the encapsulated light transmission array is 0.5 to about 5.0 mm (0.02 to about 0.2 inches). However, it is preferred that the outer dimension should be in the range from about 0.8 to about 1.5 mm (about 0.03 to about 0.06 inches), and most preferably about 1.2 mm (about 0.47 inches).

Thus, in one embodiment, the light transmission array 138 transmits the light emitted from the LED 140 to the target cells by transitioning the light through selective indices of refraction, such as from a first index of refraction $\eta 1$ of the inner encapsulant 148 to a second index of refraction $\eta 2$ of the outer encapsulant 150. By providing the catheter with a refractive index gradient in accordance with the present invention, the light may be advantageously directed more accurately and/or more efficiently toward the target cells.

Schematically shown in FIG. 6 and according to at least one embodiment, the outer encapsulant 150 includes a roughened, etched, and/or coated surface 152, generally referred to hereinafter as a roughened surface. One purpose for roughening the surface 152 of the outer encapsulant 150 is to advantageously decrease an amount of reflectance of the light that is being transmitted through the medium of the outer encapsulant 150. In turn, this permits more light to reach the target cells instead of being reflected internally back into the light transmission array 138. Another purpose for roughening the surface 152 may advantageously cause the distal end 136 of the catheter assembly 104 to be more detectable within the patient. For example, the roughened, etched, and/or coated surface 152 may be more easily detected when certain imaging techniques are employed, such as an ultrasound and/or sonic imaging technique.

In one embodiment, the surface 152 of a LED 140 package located in the distal end 136 of the catheter assembly 104 is coated by applying an echogenic polymer coating. In another embodiment, radio-opaque indicia such as, for example, metal rings or strips are arranged on the proximal end of the light bar to enhance radio-opacity. In yet another embodiment, the surface 152 is roughened by injecting gaseous bubbles just under the surface 152. It is appreciated that the surface 152 may be roughened by any one of the aforementioned embodiments or their equivalents and/or some combination thereof.

FIG. 7 schematically represents one technique of arranging a pair of LEDs 140 of the plurality of LEDs 140 of the light transmission array 138 in a flip chip configuration to decrease or lower the cross-sectional profile and/or overall thickness of the catheter assembly 104. A flip chip is one type of integrated circuit (IC) chip mounting arrangement that does not require conventional wire bonding between the chip and a substrate having a conductive trace, for example. Instead, soldered beads are deposited on the chip pads and the chip is mounted upside down in/on the substrate, hence the term "flip chip." The flip chip may be encapsulated as described above. The flip chip mounting arrangement is also referred to as Controlled Collapse Chip Connection (C4) or Direct Chip Attach (DCA).

In the embodiment shown in FIG. 7, the LEDs 140 are in communication with the power source 116 via conductive traces 154, which in turn are electrically connected to soldered bumps (not shown) formed on a substrate material 156 of the LEDs. In one embodiment, the dimensions of the LEDs are less than or equal to 0.012"×0.012" (0.3 mm×0.3 mm). In other embodiments, at least one dimension of the LEDs is less than or equal to 0.010" (0.25 mm), allowing for use of both square and rectangular LEDs. The dimensions of the LEDs are important in this type of arrangement because they, along with the encapsulation material thickness, dictate to some extent the minimum outside thickness of the catheter. In other LED arrangements, where LEDs are not "back-to-back" as in the flip chip design, the LED dimension is also important but at least the array thickness is not doubled by the back-to-back configuration.

FIG. 8 shows a top plan view of the light transmission system 100, according to one illustrated embodiment. The control module 102 includes the start/stop switch 106, the status indicator panel 110, the controller 114, and the power source 116, as described previously. Further, the control module 102 is equipped with a backing that is an adhesive patch 158. This patch 158 permits the light transmission system 100 to be at least temporarily affixed to a patient during PDT treatment.

In the illustrated embodiment, the light transmission system 100 includes a fiber optic waveguide 160 extending from the controller 114 to the distal end 136 of the catheter assembly 104. The fiber optic waveguide 160 receives at least some light that is reflected from the target cells and then transmits that light to a photodiode (not shown) that is arranged next to or in the vicinity of the controller 114. The photodiode is in communication with electro-optical circuitry to process the received light. Depending on the results of processing the received light, the controller 114 may adjust various aspects of the system 100 to enhance and/or optimize the light being transmitted to the target cells.

FIG. 9 shows an alternative embodiment of the light transmission system 100 that also includes a fiber optic waveguide 160 positioned in the distal end 136 of the catheter assembly 104. Similar to the above embodiment, the fiber optic waveguide 160 receives at least some light that is reflected from the target cells and then transmits that light to a photodiode 162 that is also located in distal end 136 of the catheter assembly 104. The photodiode 162 then sends a signal 164 to the controller 114. The signal 164 is schematically represented by the dashed line labeled as 164 in FIG. 9, but it is appreciated that the signal may travel according to a variety of transmission means, for example, over wires, cables, wireless, etc. The signal 164 may carry information regarding characteristics of the light being transmitted toward the target cells; characteristics such as the strength, intensity, efficiency, on/off or blockage status, and/or some other characteristic of the transmitted light. Upon processing the signal 164, the controller 114 may adjust various aspects of the system 100 to enhance and/or optimize the light being transmitted to the target cells. Accordingly, one purpose of the fiber optic waveguide 160 and corresponding photodiode 162 is to provide an amount of feedback to the controller 114 for real time optimization and/or adjustment of the light being transmitted toward the target cells during a PDT treatment session.

Figure 10:
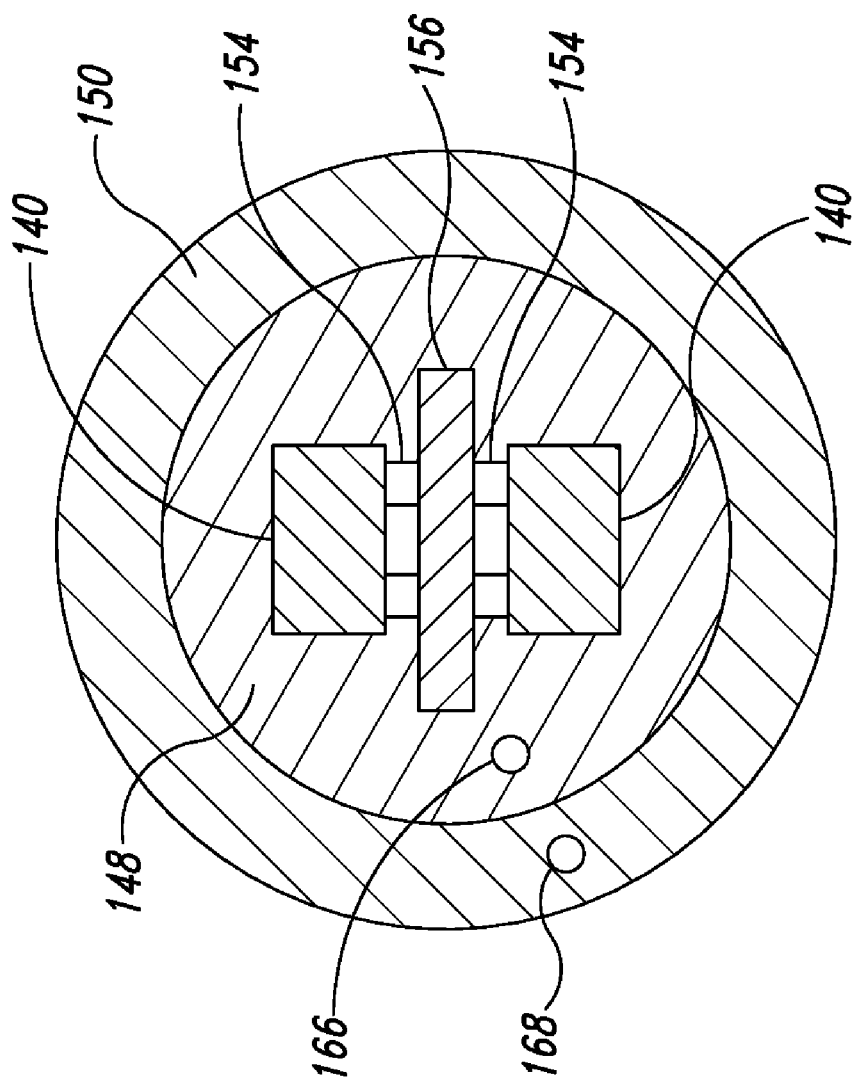
FIG. 10 is a cross-sectional view of the catheter assembly taken along line 10-10 of FIG. 4 where the catheter assembly includes internal lumens extending therethrough.

FIG. 10 shows a cross-sectional view of an embodiment of a catheter assembly, that is formed of two concentric layers of material. An optional first lumen 166 is located in the inner encapsulant 148 and an optional second lumen 168 located in the outer encapsulant 150 of the distal portion 136 of the catheter assembly 104 that is intended for insertion into the patient's body. The lumens may extend along a length of the catheter assembly to permit fluid communication between the outside and inside of the body of the patient. One, two, or more lumens may be incorporated into the catheter assembly 104 in either or both of the inner and outer encapsulants 148, 150 depending on how and where the light transmission system 100 is used.

In the illustrated embodiment, the optional first lumen 166 is a flushing lumen for providing saline or some other type of flushing fluid to the target cells and/or to the region surrounding the catheter assembly 104 before, during, and after the treatment. The first lumen 166 extends through the catheter assembly 104 and may be placed in fluid communication with a saline source. Additives can be included in the flushing fluid to enhance light transmission and dispersion relative to the target cells. Saline flushing may also be used as a way to dissipate heat generated by the LEDs.

In addition, the optional second lumen 168 is an auxiliary lumen for providing substances other than flushing fluids to the target cells. For example, the second lumen 168 may provide GELFOAM® (a product of Pharmacia Corp, Kalamazoo, Mich.), and/or fibrin glue for controlling bleeding, for example, in the region of the target cells. It is appreciated that if the catheter assembly 104 includes only the first lumen 166, then the first lumen 166 may be configured to deliver different types of substances during different times of the treatment. For example, the first lumen 166 may deliver saline to flush the site around the target cells (i.e., remove blood away from the target cells) just before treatment commences and immediately after treatment has ended. At any time before, after, or during treatment, the first lumen 166 may also deliver an amount of GELFOAM® or fibrin glue to the site around the target cells to help control bleeding.

The catheter assembly 104 may be inserted into a patient via a removeable surgical sheath.

Figure 12:
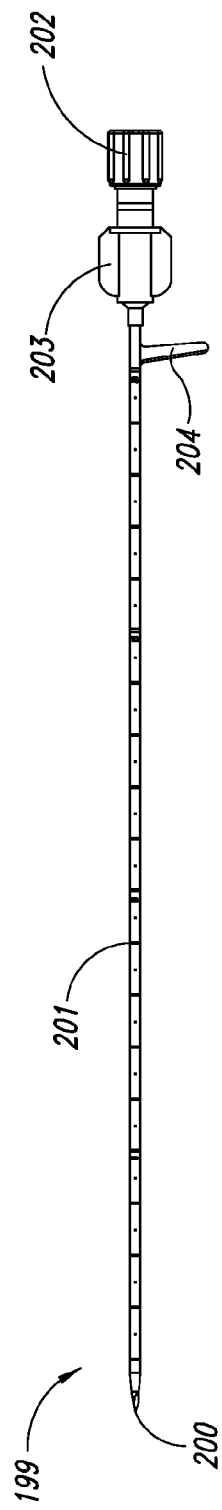
FIG. 12 is a side elevational view of an introducer provided in accordance with the present invention, illustrating a trocar and peel-away sheath.
Figure 13:
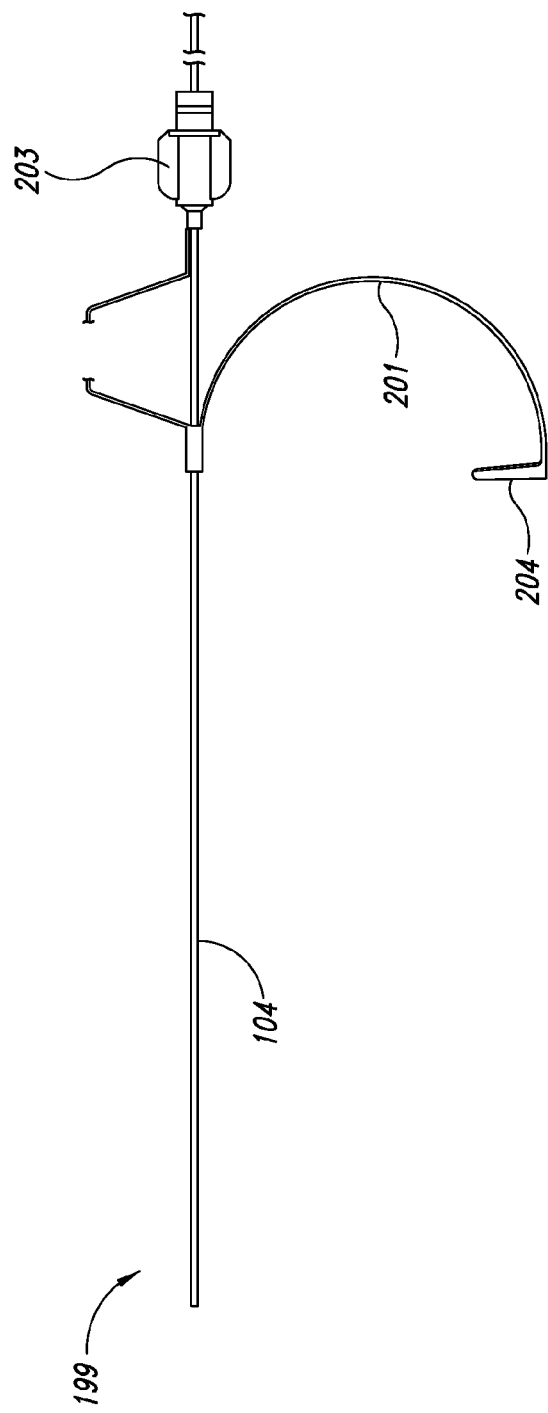
FIG. 13 is a side elevational view of the introducer of FIG. 12, with a catheter being positioned therein.

In another embodiment, as illustrated in FIG. 12, an introducer 199 provided in accordance with the present invention includes a trocar 200 and a peel-away sheath 201. While some conventional sheathes may be peeled from a very proximal end of the sheath, this is not possible if the proximal end of the sheath is contained within a Touhy-Borst valve 203, such as in the configuration illustrated in FIG. 12. However, it is beneficial and necessary to be able to peel the catheter as it is withdrawn from the patient, for example, in the situation where a distance between the patient's body and the valve is not sufficiently long to accommodate the length of the sheath that must be withdrawn to expose the catheter assembly 104 containing the LEDs.

This function is provided in accordance with the present invention by providing a handle 204 just distal to a first luer fitting 202 and valve 203, which when grasped and pulled, thereby applying a force to the handle and the sheath in a direction away from a longitudinal axis of the sheath, the sheath 201 splits and peels away from the catheter 104 while the sheath 201 is withdrawn slowly from the patient, and the catheter 104 remains stationary. In an alternative embodiment, more than one handle, for example two outward extending wing-like handles are provided, that may be pulled away from each other to split the sheath. In one embodiment, the handles are integrally formed in the sheath. In one embodiment, the sheath is formed of a flexible polymeric material having an outer diameter of about 0.08" (2.0 mm) or less, and a lumen sized to receive the catheter therein, the lumen having an inner diameter of about 0.06" (1.5 mm) or less. Furthermore, the sheath may be used to control the length of the catheter 104 and associated light source exposed within the tissue. This is accomplished by pulling the sheath 201 back by a certain distance. The sheath 201 may have markings visible to a user to indicate the insertion depth and also to indicate to a physician how much sheath has been withdrawn from the patient, and how much of the catheter contained therein has been exposed. In this manner, a catheter of a known length may be used to more effectively treat tissue regardless of location of the tissue beneath a skin surface, and to treat tissue masses of various sizes by controlling the length of exposed catheter.

In another embodiment, as illustrated in FIGS. 14-16, a trocar 200 is provided with a first luer fitting or cap 202 and a second luer cap 206. As illustrated in FIG. 15, the trocar is locked onto the sheath 201, the first luer cap 202 being fixed to the trocar needle at a proximal end. The second luer cap 206 is docked or coupled to the first luer cap 202, via a thin film tube 207. When the trocar 200 is withdrawn from the patient, the first and second luer caps are separated. While the first luer cap 202 remains at the proximal end of the trocar needle, the second luer cap 206 remains engaged with the female luer on the sheath 201. As the trocar slides out of the sheath, the thin film tubing 207 expands and extends to contain the needle and any adhered tissue, as illustrated in FIG. 16. When fully removed, the second luer cap 206 shields the sharp tip of the trocar 200. Therefore, a trocar provided in accordance with the present invention helps minimize contact between the physician and any tissue or blood of the patient and the sharp tip of the trocar.

FIGS. 17 and 18 illustrate a delivery assembly 300 that includes a needle 310 having a central lumen 312 that receives a guide wire 320. The needle 310 can be a trocar needle or other suitable device for placement of the guide wire 320. In the illustrated embodiment, the guide wire 320 extends through the needle 310 such that a distal guide wire tip 330 of the guide wire 320 extends outwardly from the a distal tip 308 of the needle 310.

To deliver a catheter assembly, the distal tip 308 of the needle 310 can be inserted into the patient's body. The guide wire 320 can be placed in the needle 310 before, during or after insertion of the needle 310. In some embodiments, the distal guidewire tip 330 is guided along the lumen 312 through the needle 310 to a position proximate the location of the targeted tissue. The needle 310 is then withdrawn from the patient, preferably while keeping the distal guide wire tip 330 within the patient. In some embodiments, the distal guide wire tip 330 is held substantially stationary while the needle 310 is slid proximally over the guide wire 320 and removed from the patient.

Once placed in the patient, the guide wire 320 defines a delivery path for advancing the catheter assembly to the targeted tissue. The guide wire 320 can be used to deliver at least an end portion of the catheter assembly into the body of the patient. In some embodiments, the guide wire 320 can be used to deliver a substantial portion of the catheter assembly into the body of the patient.

A photoactive composition can be used in combination with the delivery assembly 300. For example, an effective dose of a photoactive composition can be administered to the patient before, during and/or after inserting the needle 310 and/or the guide wire 320 into the patient.

Therefore, in accordance with the present invention, a self-contained, integrated, disposable, single use catheter is provided, integrating a light source with a power source and control circuitry. The operating parameters may be programmed into the self-contained module, or may be wirelessly programmed, allowing the user flexibility in using the light catheter for a particular treatment. By having the circuitry include a battery depletion feature, the device is safely disposed upon completion of its single use. As such, the light treatment device of the present invention is completely self-contained, sterile and programmable, providing numerous advantages over conventional systems. Furthermore, it will be understood that for ease of use, various components of the systems described herein may be packaged into a sterile surgical kit. For example, at least the control module, catheter, light bar, and surgical sheath including the trocar are enclosed within a sterile package for use by a physician. The kit may additionally or alternatively also include the drug.

In some embodiments, a single use device includes a sealed control module, catheter assembly, and a power depletion system. The sealed control module includes a power source and programmable circuitry. The catheter assembly extends from and is fused to the control module so as to form an integral unit. The catheter assembly includes an array of light transmitting devices that are in electrical communication with the power source. A power depletion system is in communication with the power source so as to selectively deplete energy from the power source.

In some embodiments, the catheter assembly has an outside dimension of from about 0.8 mm to about 1.5 mm. In other embodiments, the catheter assembly has an outside dimension of about 1.2 mm. In some embodiments, the light transmitting devices are LED die that have a dimension in the size range from about 0.152 mm to about 0.304 mm.

In some embodiments, the array comprises an array of LEDs. The array is capable of emitting from about 5 mW to about 50 mW per centimeter of array length. In some embodiments, the control module is configured to pulse the array of light emitters according to a frequency or according to a timed pattern. In some embodiments, the light transmitting devices emit about 80% of light within a range of 20 nm around an activation wavelength of a photoactive composition. In some embodiments, the activation wavelength is about 664 nm.

In some embodiments, the device also includes a deactivation module, which is located in either the control module or the catheter. The deactivation module includes electronic circuitry or a chemical fuse. In some embodiments, the control module is hermetically sealed and lacks access to recharge the power source or induction recharge capability. In some embodiments, the power source is non-rechargeable.

In some embodiments, a plurality of radio-opaque indicia are associated with a portion of the catheter assembly that is inserted into a body of a patient when the device is in use.

In some embodiments, the device includes an adhesive patch on a patient-facing side of the control module to adhere the control module to a patient.

In some embodiments, the device includes a first material surrounding at least a portion of the light transmission array. The first material has a first refractive index. A second material has a second refractive index and surrounds the first material. The second refractive index is less than the first refractive index. In some embodiments, the first refractive index is in the range from about 1.51 to about 2.0, and the second refractive index is in the range from about 1.33 to about 1.5.

In some embodiments, the catheter assembly includes at least one lumen that extends along its length. The at least one lumen is adapted for transmitting a fluid between a location outside a body of a patient and a location inside the body of the patient.

In some embodiments, the light transmission array is encapsulated within the catheter assembly. The light transmission array is in electrical communication with the power source and has an operational frequency in the range from about 50 Hz to about 5 kHz.

In some embodiments, a device includes a sealed control module, flexible catheter assembly, and deactivation module. The sealed control module includes a power source and electronic circuitry in electrical communication with the power source. The flexible catheter assembly extends from the control module and forms an integral unit with the control module. The catheter assembly also includes an array of light transmitting devices. The deactivation module selectively disables the device.

In some embodiments, the deactivation module includes electronic circuitry or a chemical fuse. The electronic circuitry or a chemical fuse is triggerable so as to disable the control module. In some embodiments, the deactivation module includes electronic circuitry that is configured to selectively and temporarily disable controls of the control module. In some embodiments, the deactivation module is located in the catheter assembly. When activated, the deactivation module includes a chemical fuse, which is configured to disrupt electrical communication from the power source to the light transmitting devices in the catheter assembly.

In some embodiments, the light transmitting devices are LED die in the size range from about 0.152 mm to about 0.304 mm. The array provides from about 20 mW to about 50 mW per centimeter of array length, when the device is in use.

In some embodiments, a first material surrounds at least a portion of the light transmission array. The first material has a first refractive index. A second material has a second refractive index. The second material surrounds the first material. The second refractive index is less than the first refractive index. In some embodiments, the first refractive index is in the range from about 1.51 to about 2.0. The second refractive index is in the range from about 1.33 to about 1.5.

In some embodiments, the catheter assembly includes at least one lumen that extends along a length of the catheter assembly. The at least one lumen is adapted for transmitting a fluid between a location outside a body of a patient and a location inside the body of the patient when the device is in use.

In some embodiments, the light transmission array is encapsulated within the catheter assembly and in electrical communication with the power source. The array has an operational frequency in the range from about 50 Hz to about 5 kHz.

In some embodiments, the control module is configured to pulse the light array of light emitters according to a frequency or according to a timed pattern.

In some embodiments, the device includes a plurality of radio-opaque indicia associated with a portion of the catheter assembly that is inserted into a body of a patient when the device is in use.

In some embodiments, the device includes an adhesive patch on a patient-facing side of the control module to adhere the control module to a patient.

In some embodiments, the catheter assembly has an outside dimension of from about 0.8 mm to about 1.5 mm. In other embodiments, the catheter assembly has an outside dimension of about 1.2 mm.

In some embodiments, the control module is hermetically sealed and lacks access to recharge the power source or induction recharge capability. In some embodiments, the power source is non-rechargeable.

In some embodiments, a sterile, packaged surgical kit is provided for administering photoreactive therapy to a patient. The kit includes a portable, single use, sealed control module and polymeric, flexible catheter assembly. The control module has a power source and control circuitry in communication with the power source. The catheter assembly extends from a first end to the second end. The first end of the catheter assembly is fused to the control module. A light transmission array is encapsulated in the second end. The transmission array is in electrical communication with the power source. The transmission array includes a plurality of LEDs. The catheter assembly has an outer dimension of about 0.8 to about 1.5 mm, and the LEDs have a height in the range from about 0.152 mm to about 0.304 mm. The kit further includes a surgical sheath and container. The surgical sheath includes a lumen adapted to receive the catheter assembly and is formed from a flexible polymeric material. The sheath has a lumen of an inner diameter sized for receiving a portion of the catheter assembly. The container includes a quantity of a photoreactive agent mono-L-aspartyl chlorin e6 sufficient to administer a single dose to a patient. At least the control module, catheter assembly, and surgical sheath are enclosed within a sterile package.

In some embodiments, the kit further includes a discharge module to selectively discharge the power source to prevent reuse of the control module after a single use.

In some embodiments, the deactivation module includes electronic circuitry or chemical fuse. The deactivation module is triggerable to disable the control module.

In some embodiments, the kit further includes a trocar enclosed within a sterile package.

In some embodiments, the catheter assembly has an outside dimension of from about 0.8 mm to about 1.5 mm. In other embodiments, the catheter assembly has an outside dimension of about 1.2 mm.

In some embodiments, the light transmitting devices are LED die that have a dimension in the size range from about 0.152 mm to about 0.304 mm. In some embodiments, the array includes an array of LEDs. The array is capable of emitting from about 5 mW to about 50 mW per centimeter of array length. In some embodiments, the array includes LEDs that provide from about 20 mW to about 50 mW per centimeter of array length, when the device is in use.

In some embodiments, the control module is hermetically sealed and lacks access to recharge the power source or induction recharge capability. In some embodiments, the power source is non-rechargeable. In some embodiments, a plurality of radio-opaque indicia are associated with a portion of the catheter assembly that is inserted into a body of a patient when the device is in use.

In some embodiments, the kit further comprises a first material that surrounds at least a portion of the light transmission array. The first material has a first refractive index. A second material has a second refractive index and surrounds the first material. The second refractive index is less than the first refractive index. In some embodiments, the first refractive index is in the range from about 1.51 to about 2.0, and the second refractive index is in the range from about 1.33 to about 1.5.

In some embodiments, the catheter assembly includes at least one lumen that extends along a length of the catheter assembly. The at least one lumen is adapted for transmitting a fluid between a location outside a body of a patient and to a location inside the body of the patient when the device is in use.

In some embodiments, the sheath includes an introduced parting line along its length. The sheath also has an outward extending member that is configured for manual grasping and pulling so as to split the sheath along the parting line.

In some embodiments, the container includes a sufficient mono-L-aspartyl chlorin e6 for a dose of at least 1.01 mg/kg of patient body mass.

In some embodiments, a method of administering photoactive therapy to treat abnormal tissue of a human or non-human patient is provided. The method includes identifying a location of abnormal tissue to be treated. A trocar is transcutaneously inserted into a body of the patient. The trocar is disposed within a surgical sheath. The sheath is guided to a position proximate the location of the abnormal tissue. The trocar is then withdrawn from the sheath while retaining the sheath in a desired position. An effective dose of a photoactive composition is administered to the patient. In some embodiments, at least an end portion of a catheter assembly is inserted into the sheath and has a light transmission array. The catheter assembly is fused to a sealed single use control module. The control module has a power source and control circuitry configured to carryout a treatment protocol. The control module is activated after confirming placement of the light transmission array of the catheter assembly relative to abnormal tissue to be treated. The light treatment is automatically terminated after a predetermined period of treatment.

In some embodiments, the module is activated by activating the light transmission array so as to deliver about 50 to about 1000 J/cm of array length at about 5 to about 50 mW/cm of array length to the selected location over a period of about 15 minutes to about 60 hours. In other embodiments, the module is activated by activating the light transmission array to deliver about 50 to about 500 J/cm of array length at about 20 to about 50 mW/cm of array length.

In some embodiments, the control module and/or catheter assembly are automatically and permanently disabled after termination of treatment. In some embodiments, the power source is automatically drained upon automatically terminating.

In some embodiments, a fluid is delivered through a lumen in the catheter assembly from a location external to the patient to a location within the patient. In some embodiments, GEL-FOAM® or fibrin glue is delivered through the lumen.

In some embodiments, the controls provided on the control module are selectively and temporarily disabled during a predetermined time period that the light transmission array is activated.

In some embodiments, the end portion of the catheter assembly has an outside dimension of about 1.2 mm.

In some embodiments, the step of administering a photoactive agent includes administering mono-L-aspartyl chlorin e6. The photoactive agent is administered at about 1.0 mg/kg of patient body mass.

In some embodiments, the array is activated to produce 80% of energy at a wavelength of 664 nm+/−20 nm.

In some embodiments, an imaging apparatus able to image the trocar position is used to guide the catheter assembly. In some embodiments, the imaging apparatus is used to confirm the position of the catheter assembly.

In some embodiments, a method of administering photoactive therapy to treat targeted tissue of a human or non-human patient is provided. The method includes identifying a location of targeted tissue to be treated. A needle Is transcutaneously inserting into a body of the patient. The needle has a central lumen sized to accept a guide wire. The lumen also guides a distal guide wire tip to a position proximate the location of the targeted tissue. The needle is withdrawn from the patient while retaining the guide wire tip in position. An effective dose of a photoactive composition is administered to the patient before, during and/or after inserting the needle. At least an end portion of a catheter assembly is guided via the guide wire into the body of the patient. The catheter assembly is fused to a sealed single use control module. The control module includes a power source and control circuitry configured to carryout a treatment protocol. The catheter assembly end portion includes a light transmission array. The control module is activated after confirming placement of the light transmission array of the catheter assembly relative to abnormal tissue to be treated. The light treatment is automatically terminated after a predetermined period of treatment.

The above description of illustrated embodiments, including what is described in the Abstract, is not intended to be exhaustive or to limit the invention to the precise forms disclosed. Although specific embodiments of and examples are described herein for illustrative purposes, various equivalent modifications can be made without departing from the spirit and scope of the invention, as will be recognized by those skilled in the relevant art. The teachings provided herein of the invention can be applied to various light transmission devices and/or systems, not necessarily the light transmission systems generally described above.

Aspects of the invention can be modified, if necessary, to employ aspects, features, and concepts of the various patents, applications, and publications to provide yet further embodiments of the invention. These and other changes can be made to the invention in view of the above-detailed description. In general, in the following claims, the terms used should not be construed to limit the invention to the specific embodiments disclosed in the specification and the claims, but should be construed to include all light transmission systems that operate in accordance with the claims. Accordingly, the invention is not limited by the disclosure, but instead its scope is to be determined entirely by the following claims.

The invention claimed is:

1. A single use device, comprising:
a control module comprising a power source and circuitry; and
a catheter assembly permanently coupled to the control module, the catheter assembly comprising energy emitting devices in electrical communication with the power source, the energy emitting devices being configured to output energy to a subject to perform therapy, the circuitry being configured to make both the control module and the catheter assembly inoperable after a single use to prevent energy from being outputted from the energy emitting devices to the subject.

2. The single use device of claim 1 wherein the circuitry includes software configured to perform a self-erase function at an end of therapy.

3. The single use device of claim 2 wherein the circuitry is configured to discharge the power source after the self-erase function is performed.

4. The single use device of claim 1 wherein the circuitry is programmed to delete executable instructions to render the control module inoperable after the single use.

5. The single use device of claim 1 wherein the circuitry is configured to completely discharge or deplete the power source after completion of therapy.

6. The single use device of claim 1, further comprising a fuse that disables the single use device.

7. A single use device, comprising:
a control module comprising a power source and circuitry;
a catheter assembly permanently coupled to the control module, the catheter assembly comprising at least one energy emitting device configured to be in electrical communication with the power source; and
a deactivation module, the deactivation module and the control module are configured to cooperate to selectively disable the single use device to prevent reuse of the control module and reuse of the catheter assembly.

8. The single use device of claim 7 wherein the deactivation module comprises a chemical fuse in the catheter assembly, the fuse is configured when activated to disrupt electrical communication from the power source to the at least one energy emitting device.

9. The single use device of claim 7 wherein the circuitry includes programmed instructions to perform a self-erase function at an end of therapy.

10. The single use device of claim 9 wherein the circuitry is programmed to discharge the power source after performing the self-erase function.

11. The single use device of claim 7 wherein the circuitry is configured to completely discharge or deplete the power source prior to delivering all of the energy in the power source to the catheter assembly.

12. The single use device of claim 7 wherein the power source is capable of outputting a sufficient amount of electrical energy to destroy at least a portion of the single use device to prevent reuse of the control module and to prevent reuse of the catheter assembly.

13. The single use device of claim 12, further comprising a fuse which is destroyed by the electrical energy outputted by the power source.

14. The single use device of claim 13 wherein the fuse is configured when activated to disrupt electrical communication from the power source to at least one energy emitting device.

15. The single use device of claim 7 wherein the control module further comprises controls, and the electronic circuitry is configured to selectively disable the controls of the control module.

16. The single use device of claim 7 wherein the control module and the catheter assembly form an integral unit.

17. The single use device of claim 7, wherein the circuitry is automatically destroyed at an end of therapy.

* * * * *